United States Patent
Bushweller et al.

(10) Patent No.: US 11,241,421 B2
(45) Date of Patent: Feb. 8, 2022

(54) COMBINATION THERAPIES FOR TREATING CANCER

(71) Applicant: UNIVERSITY OF VIRGINIA PATENT FOUNDATION, Charlottesville, VA (US)

(72) Inventors: John H. Bushweller, Crozet, VA (US); Anuradha Illendula, Crozet, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 0 days.

(21) Appl. No.: 16/318,041

(22) PCT Filed: Jul. 27, 2017

(86) PCT No.: PCT/US2017/044124
§ 371 (c)(1),
(2) Date: Jan. 15, 2019

(87) PCT Pub. No.: WO2018/022855
PCT Pub. Date: Feb. 1, 2018

(65) Prior Publication Data
US 2019/0343820 A1  Nov. 14, 2019

Related U.S. Application Data

(60) Provisional application No. 62/367,263, filed on Jul. 27, 2016.

(51) Int. Cl.
*A61K 31/4439* (2006.01)
*A61P 35/02* (2006.01)
*A61K 31/704* (2006.01)

(52) U.S. Cl.
CPC ........ *A61K 31/4439* (2013.01); *A61K 31/704* (2013.01); *A61P 35/02* (2018.01)

(58) Field of Classification Search
None
See application file for complete search history.

(56) References Cited

U.S. PATENT DOCUMENTS

| 5,643,935 | A | 7/1997 | Dykstra et al. | |
| 6,372,719 | B1 * | 4/2002 | Cunningham | A61P 9/00 514/34 |
| 2008/0161252 | A1 | 7/2008 | Reddy et al. | |
| 2014/0243331 | A1 | 8/2014 | Bushweller et al. | |

OTHER PUBLICATIONS

International Search Report and Written Opinion in International Application No. PCT/US2017/044124, dated Nov. 17, 2017.
Dombret and Gardin "An update of current treatments for adult acute myeloid leukemia", Blood, Jan. 7, 2016, vol. 127, No. 1, pp. 53-61.
Illendula et al., "A small-molecule inhibitor of the aberrant transcription factor CBF beta-SMMHC delays leukemia in mice", Science, vol. 347, No. 6223, Feb. 13, 2015, pp. 779-784.
Pulikkan et al., "Selective Inhibition of the Leukemia Fusion Protein CBF beta-SMMHC by Small Molecule Al-10-49 in the treatment of Inv(16) AML", Blood, vol. 124. No. 21, Dec. 2014; Abstract, 56th Annual Meeting of the American Society of Hematology; San Francisco, Dec. 6, 2014.
Law et al., "Improved Prognostic Significance of t(8:21) Karyotype in Acute Myeloid Leukaemia," Indian J Hematol Blood Transfus (Oct.-Dec. 2011) 27(4): 185-289; DOI 10.1007 / sl2288-011-0125-8, p. 273, Abstract p. 285.
Pulikkan et al., "Selective inhibition of the leukemia fusion protein CBFβ-SMMHC by small molecule Al-10-49 in the treatment of Inv(16) AML," Blood, & 56th Annual Meeting of the American-Society-of-Hematology; San Francisco, CA, USA; Dec. 6-9, 2014, (Dec. 2014), vol. 124, No. 21.

* cited by examiner

*Primary Examiner* — Layla D Berry
(74) *Attorney, Agent, or Firm* — J.A. Lindeman & Co. PLLC

(57) ABSTRACT

This invention relates to methods and compositions for treatment of inv(16) leukemia and particularly to treatment of acute myeloid leukemia. Disclosed is a method of treating inv(16) leukemia comprising the step of administering to a subject in need thereof a therapeutically effective combination of a) a compound of the formula (1) and b) a chemotherapeutic agent selected from the group consisting of pirarubicin, aclarubicin, mitoxantrone, doxorubicin, daunorubicin, idarubicin, epirubicin, cytarabine, pharmaceutically acceptable salts and mixtures thereof. The therapeutically effective combination synergistically inhibits proliferation of inv(16) leukemia cells. This invention also relates to pharmaceutical compositions comprising a therapeutically effective combination of the compound of formula (1) and the chemotherapeutic agent and a pharmaceutically acceptable excipient.

(1)

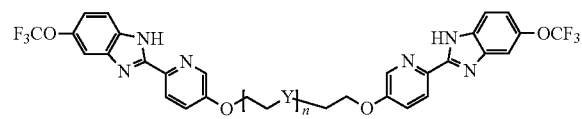

26 Claims, 5 Drawing Sheets

COMBINATION THERAPIES FOR TREATING CANCER

CROSS-REFERENCE TO RELATED APPLICATIONS

This application claims priority to U.S. Application No. 62/367,263, filed Jul. 27, 2016, which is incorporated herein by reference.

STATEMENT REGARDING FEDERALLY SPONSORED RESEARCH OR DEVELOPMENT

This invention was made with government support under Grant Nos. CA108056 and CA140398, awarded by the National Institutes of Health. The government has certain rights in the invention.

FIELD OF THE INVENTION

The invention generally relates to compositions and methods to treat leukemia. More particularly, the invention relates to compositions and methods of treatment using a synergistic combination of chemotherapeutic agents and specific transcription factor inhibitors.

BACKGROUND OF THE INVENTION

Acute myeloid leukemia (AML) is the most common form of adult leukemia. The transcription factor fusion CBFβ-SMMHC (core binding factor β and the smooth-muscle myosin heavy chain), expressed in AML with the chromosome inversion inv(16)(p13q22), outcompetes wild-type CBFβ for binding to the transcription factor RUNX1, deregulates RUNX1 activity in hematopoiesis, and induces AML. Current inv(16) AML treatment with nonselective cytotoxic chemotherapy results in a good initial response but limited long-term survival.

CBF is a heterodimeric transcription factor composed of a DNA-binding RUNX subunit (encoded by one of three genes: RUNX1, RUNX2, or RUNX3) and a non-DNA-binding CBFβ subunit, which increases the affinity of RUNX proteins for DNA. All three RUNX proteins as well as CBFβ have been shown to be critical regulators of specific developmental pathways. RUNX1 and CBFβ are essential for definitive hematopoiesis, where they regulate expression of genes associated with proliferation, differentiation, and survival of stem and progenitor cells. RUNX2 is essential for normal bone formation by way of transcriptional regulation of genes critical for bone development. Both RUNX1 and RUNX3 play key roles in neuronal development.

Based on their critical roles in normal development, RUNX proteins and CBFβ are targets of alteration in a number of cancers. Both RUNX1 and CBFβ undergo chromosomal translocations in a subset of acute myeloid leukemia (AML) and acute lymphocytic leukemia (ALL) patients where the corresponding fusion proteins have clearly been shown to be drivers of disease. For the fusion proteins AML1-ETO and TEL-AML1, the binding of the fusion proteins to CBFβ has been shown to be essential for transformation. RUNX1 is mutated in a subset of AML and myelodysplastic syndrome (MDS) patients.

Small molecule inhibitors of protein-protein interactions, particularly in the context of transcription factors, is still a relatively nascent field, in part due to the long and widely held belief that this class of interactions is "undruggable," i.e., targeting such interactions would have a very low likelihood of success. With an increasing number of success stories of small molecule inhibitors affecting protein-protein interactions, including transcription factors, this paradigm is clearly changing. In addition, the recent development of small molecule inhibitors of epigenetic signaling proteins, such as the BRD4 or EZH2 inhibitors, clearly indicate that small molecule modulation of transcription, in particular, is a potentially powerful approach to cancer treatment.

U.S. Pat. Nos. 8,748,618 and 9,221,764, incorporated herein by reference, report small molecule inhibitors of the protein-protein interaction between CBFβ-SMMHC and the Runt domain of RUNX1 which bind to the CBFβ portion of CBFβ-SMMHC. Dimeric inhibitors disclosed in U.S. Pat. Nos. 8,748,618 and 9,221,764 show increased potency against inv(16) cell lines and minimal effect on non inv(16) cell lines.

Patients with inv(16) AML usually undergo aggressive chemotherapy regimens involving cytotoxic drugs such as Ara-C and anthracyclines. This treatment is better tolerated by young patients showing a 5 year overall survival of 45% to 65% (Ravandi, et al., 2007; Pulsoni, et al., 2008). However, most patients are older and the 5-year overall survival for patients older than 60 years old is about 20% (Farag, et al., 2006). These data indicate targeted therapies that can improve the therapeutic response for inv(16) AML patients are desired.

Emerging literature suggests that inability to cure cancers with current therapies, including cytotoxic chemotherapy, kinase inhibitors, or monoclonal antibodies, may be attributed to a population of so-called cancer stem cells or cancer initiating cells that are resistant to treatment, are quiescent, have long term self-renewal potential, and can fully recapitulate tumor phenotype at time of relapse. Inv(16) AML is a good example of this failure because inv(16) patients invariably show, at time of relapse, the inv(16) rearrangement, although other mutations detected at diagnosis (RAS, FLT3ITD or KIT) may or may not be detected at relapse (Nakano, et al., 1999; Kottaridis, et al., 2002; Shih, et al., 2008).

Currently, standard cytotoxic chemotherapy is used for the treatment of inv(16) leukemia. While reasonably well tolerated by younger patients, this is not well tolerated by the predominantly older patient population afflicted by this disease. More importantly, approximately 60% of inv(16) patients relapse and die within 5 years, indicating a substantial relapse rate. This is likely the result of not eradicating the leukemia stem cell population when treating with standard chemotherapy, allowing the disease to recur. As it is known that CBFβ-SMMHC changes the gene expression profile of cells to something that is more stem cell like, it is clear that CBFβ-SMMHC is a driver of the leukemia stem cell phenotype. Therefore, it is highly likely that direct inhibition of CBFβ-SMMHC can alter this expression profile and therefore be a more effective therapeutic approach either alone or in combination with cytotoxic chemotherapy.

There is a long felt need in the art for compositions and methods useful for preventing and for treating acute myeloid leukemia, particularly involving the inv(16) fusion. The present invention satisfies these needs.

SUMMARY OF THE INVENTION

This invention generally relates to methods and compositions for treatment of inv(16) leukemia.

This invention relates to a method of treating inv(16) leukemia comprising the step of: administering to a subject in need thereof a therapeutically effective combination of
a) a compound of the formula (1)

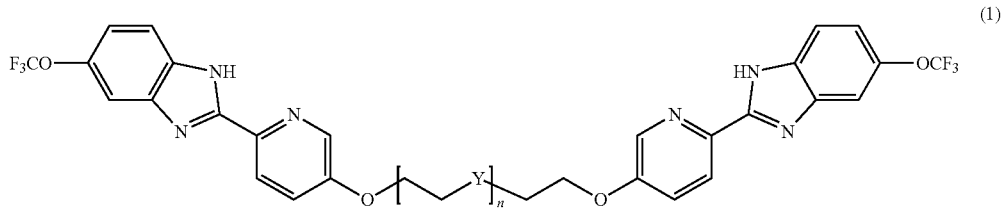

where Y is O, NH, or NR where R is methyl or ethyl,
where n is an integer of from 1 to 10,
or a pharmaceutically acceptable salt thereof; and
b) a chemotherapeutic agent selected from the group consisting of pirarubicin, aclarubicin, mitoxantrone, doxorubicin, daunorubicin, idarubicin, epirubicin, cytarabine, pharmaceutically acceptable salts and mixtures thereof. The therapeutically effective combination of the compound of formula (1) and the chemotherapeutic agent synergistically inhibits proliferation of inv(16) leukemia cells.

In methods according to the invention, compounds of formula (1) and the chemotherapeutic agent are administered simultaneously, or sequentially by first administering the compound of formula (1) followed by administering the chemotherapeutic agent.

This invention also relates to pharmaceutical compositions comprising a therapeutically effective combination of the compound of formula (1) and the chemotherapeutic agent and a pharmaceutically acceptable excipient. The therapeutically effective combination of the compound of formula (1) and the chemotherapeutic agent is a combined amount synergistically effective to inhibit proliferation of inv(16) leukemia cells.

In the methods and pharmaceutical compositions of the invention, the compound of formula (1) is a compound of formula (1a) or a pharmaceutically acceptable salt thereof,

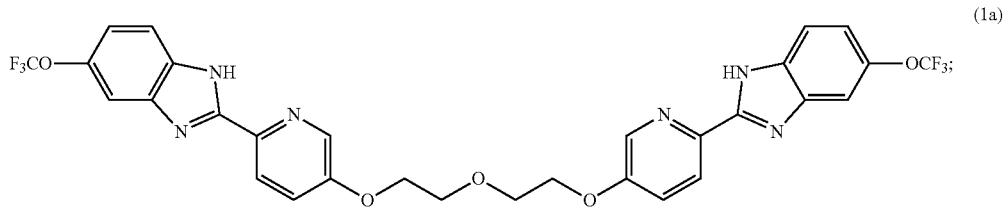

and the chemotherapeutic agent is doxorubicin or a pharmaceutically acceptable salt thereof

DETAILED DESCRIPTION

Figure 1:
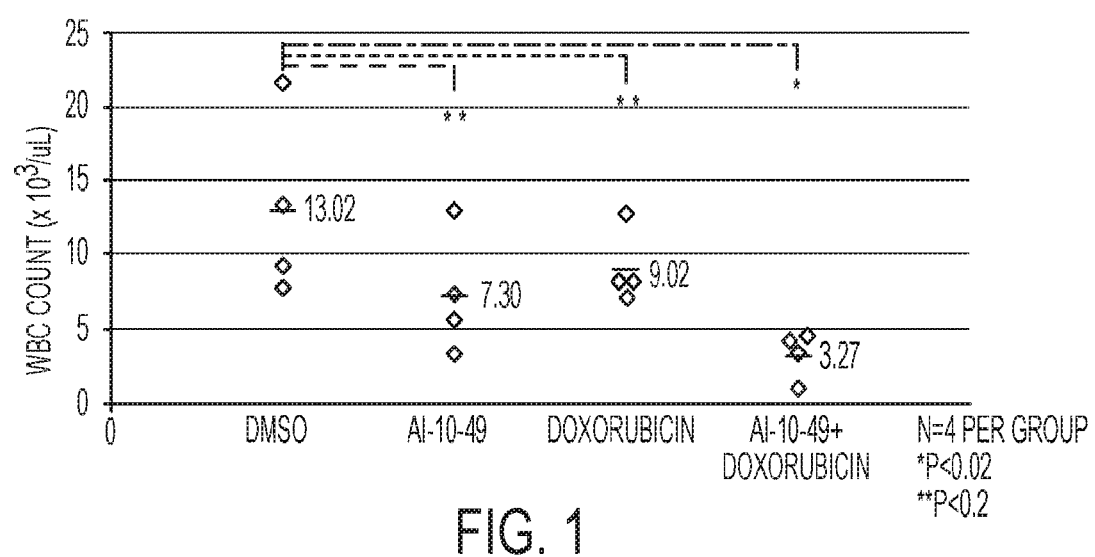
FIG. 1. Measurement of white blood cell count from mice transplanted with leukemia and treated with DMSO (control), doxorubicin, AI-10-49, and Doxorubicin+AI-10-49.

The invention relates to methods of treatment of inv(16) leukemia comprising administering to a subject in need thereof a therapeutically effective combination of:
a) a compound of formula (1)

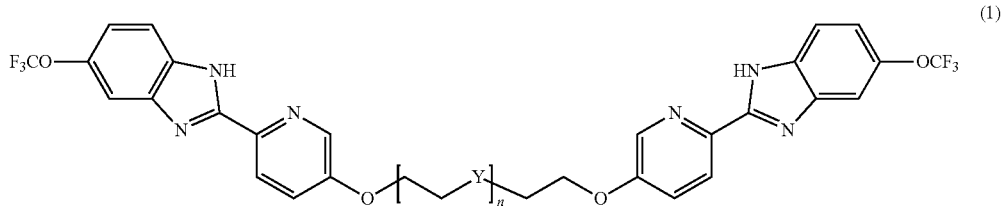

where Y is O, NH, or NR where R is methyl or ethyl, where n is an integer of from 1 to 10, or a pharmaceutically acceptable salt thereof; and
b) a chemotherapeutic agent selected from the group consisting of pirarubicin, aclarubicin, mitoxantrone, doxorubicin, daunorubicin, idarubicin, epirubicin and cytarabine, and mixtures thereof, or a pharmaceutically acceptable salt thereof.

The therapeutically effective combination of the compound of formula (1) and the chemotherapeutic agent synergistically inhibits proliferation of inv(16) leukemia cells. The method of the invention is particularly useful in the treatment of acute myeloid leukemia, one type of inv(16) leukemia. "Treatment" or "treating" includes prophylaxis of the specific disorder or condition, or alleviation of the symptoms associated with a specific disorder or condition and/or preventing or eliminating those symptoms.

Surprisingly, a synergistic effect is seen when certain combined amounts of compounds of formula (1) and a chemotherapeutic agent are used to inhibit the proliferation of inv(16) leukemia cells. The synergistic combination used in the invention has a weight to weight ratio of the daily administered dose of chemotherapeutic agent to the daily administered dose of compounds of formula (1) ranging from about 0.0001:1 to about 1000:1. The ratio may be from about 0.001:1 to about 100:1, e.g., from about 0.01:1 to about 10:1, e.g. from about 0.1:1 to about 1:1.

Direct inhibition of the oncogenic CBFβ-SMMHC fusion protein has been shown as a potentially effective therapeutic approach for inv(16) AML. (Illendula, et al., 2015.) 5-methoxy-2-(pyridin-2-yl)-1H-benzo[d]imidazole, AI-4-57, was reported as a compound which binds to the CBFβ portion of the CBFβ-SMMHC fusion protein and inhibits its binding to the Runt domain of RUNX proteins (Illendula, et al., 2015.) The trifluoromethoxy (CF₃O) derivative, 2-(pyridin-2-yl)-5-(trifluoromethoxy)-1H-benzo[d]imidazole, A-10-47 displayed enhanced metabolic stability relative to the methoxy compound. (Illendula, et al., 2015.) Polyethylene glycol-based linkers were used to create bivalent derivatives with 5-, 7-, 10-, and 16-atom linker lengths. (Illendula, et al., 2015.) The five-atom linker compound had less activity, but the longer linker compounds show potent inhibition. A compound with a seven-atom linker, AI-4-83, displayed a 63-fold enhancement over the monovalent compound. In addition, AI-4-83 achieved >10-fold dissociation of CBFβ-SMMHC and RUNX1 Runt domain at saturating concentrations. (Illendula, et al., 2015.)

The trifluoromethoxy derivative with a seven-atom linker, AI-10-49, also referred to herein as compound (1a),

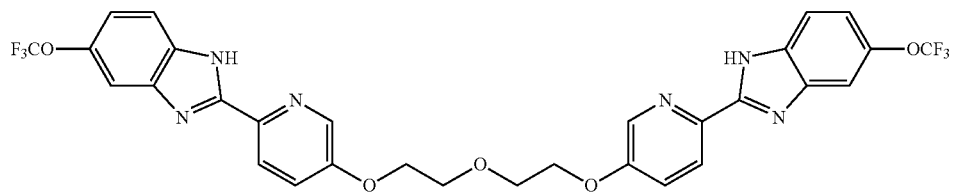 [SMILES: FC(F)(F)Oc1ccc2[nH]c(-c3ccc(OCCOCCOc4ccc(-c5nc6cc(OC(F)(F)F)ccc6[nH]5)nc4)cn3)nc2c1]

was shown to be a potent and CBFβ-SMMHC specific compound that induced cell death in the ME-1 cell line, a leukemia cell line with inv(16). (Illendula, et al., 2015.) CBFβ-SMMHC is oligomeric, whereas CBFβ is monomeric. AI-10-49 inhibits CBFβ-SMMHC activity while having a minimal effect on CBFβ function. (Illendula, et al., 2015.)

In methods according to the invention, compounds of formula (1) contain two 2-(pyridin-2-yl)-5-(trifluoromethoxy)-1H-benzo[d]imidazole groups, attached by a linker, —O—[CH₂CH₂Y]ₙ—O—. In compounds of formula (1), the linker connects the two binding portions of the molecule through the benzimiadazole rings. Dimeric or bivalent inhibitors take advantage of the oligomeric nature of CBFβ-SMMHC and apply the principles of poly-valency (Mammen, et al., 1998; Kiessling, et al., 2006) to achieve the desired selectivity. The truncated forms of CBFβ-SMMHC lacking the extreme C-terminus have been shown to form dimers in solution. (Lukasik, et al., 2002.) For the full-length protein, these dimers then oligomerize to form high order oligomers. (Shigesada, et al. 2004.) In contrast, CBFβ is monomeric in solution. This difference in oligomerization provides a means to achieve selective inhibition of CBFβ-SMMHC versus CBFβ.

According to methods of the invention, in compounds of formula (1), Y is O, NH, or S. In a method of the invention, Y is O. In another method of the invention, Y is N—CH$_3$. When n is greater than 1, Y can be the same or different.

According to methods of the invention, in compounds of formula (1), n is an integer from 1 to 10. In methods and compositions according to the invention, n is 1, 2, 3, 4, 5, 6, 7, 8, 9, or 10. Preferably, n is from 1 to 5. In compounds of formula (1), the linker should be long enough to allow the bivalent compound of formula (1) to achieve binding enhancement by means of CBFβ-SMMHC-ligand interaction versus a mono-valent CBFβ-ligand interaction. See U.S. Pat. No. 9,221,764, FIG. 5. The dissociation constant for a monovalent compound binding to monomeric CBFβ is equal to K$_d$(monomer). A homo-dimer of this compound will bind the monomeric CBFβ protein with a dissociation constant equal to K$_d$(monomer)/2. However, this same homo-dimer will interact with two sites on the dimeric CBFβ-SMMHC protein and have a K$_d$(dimer) equal to (K$_d$(monomer))$^2$/C$_{eff}$ where C$_{eff}$ is the effective concentration resulting from the tethering of the two binding sites on CBFβ-SMMHC to one another. (Mulder, et al., 2004)

Non-limiting exemplary compounds within formula (1), include:

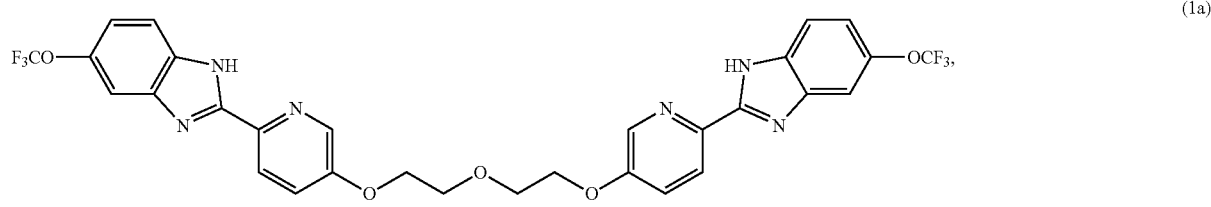

(1a)

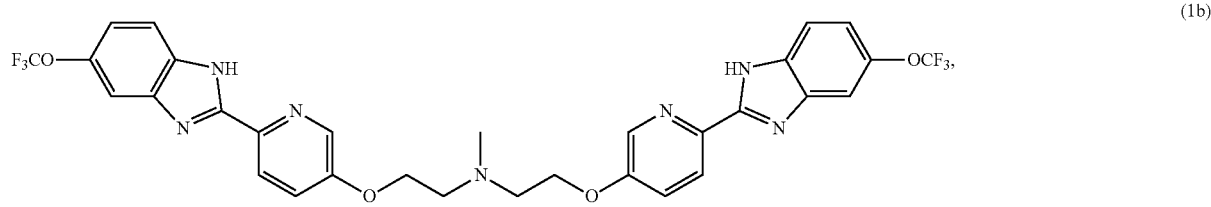

(1b)

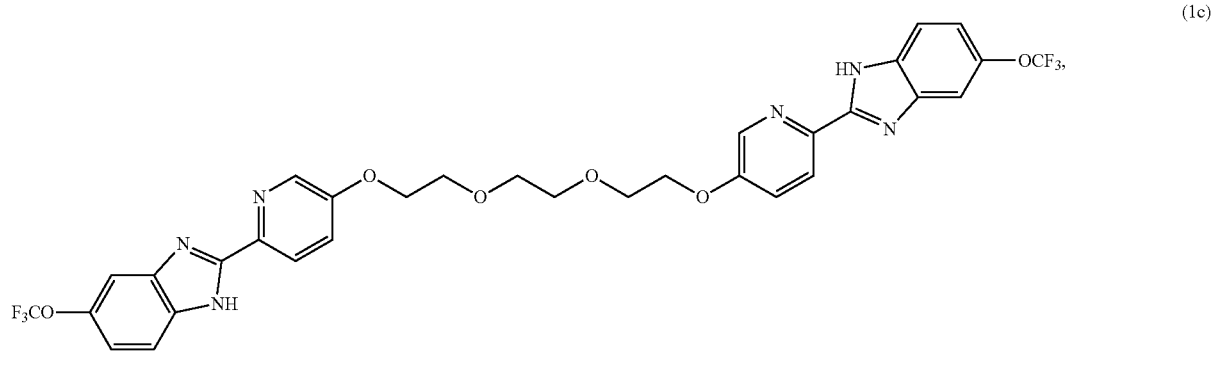

(1c)

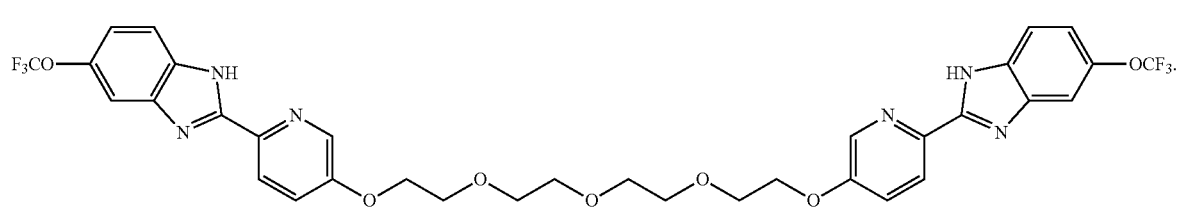

(1d)

In a preferred method according to the invention, the compound of formula (1) is

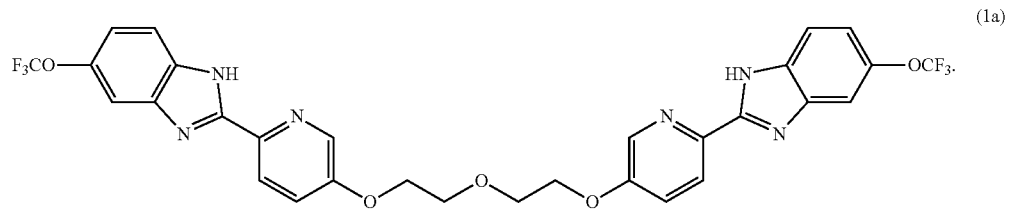 [SMILES: FC(F)(F)Oc1ccc2[nH]c(-c3ccc(OCCOCCOc4ccc(-c5nc6cc(OC(F)(F)F)ccc6[nH]5)nc4)cn3)nc2c1]

(1a)

U.S. Pat. No. 9,221,764, incorporated herein by reference, discloses structures and synthetic routes of specific bivalent inhibitors with polyethylene glycol-based linkers.

In a method according to the invention, the compound of formula (1) is organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

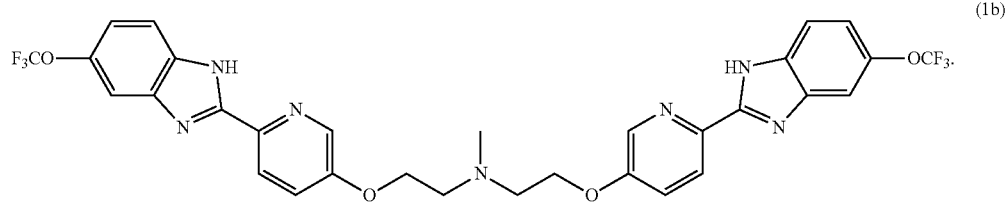

(1b)

An exemplary synthesis of compound (1b), also known as AI-14-124, is shown below:

Patients with inv(16) AML usually undergo aggressive chemotherapy regimens involving cytotoxic drugs such as

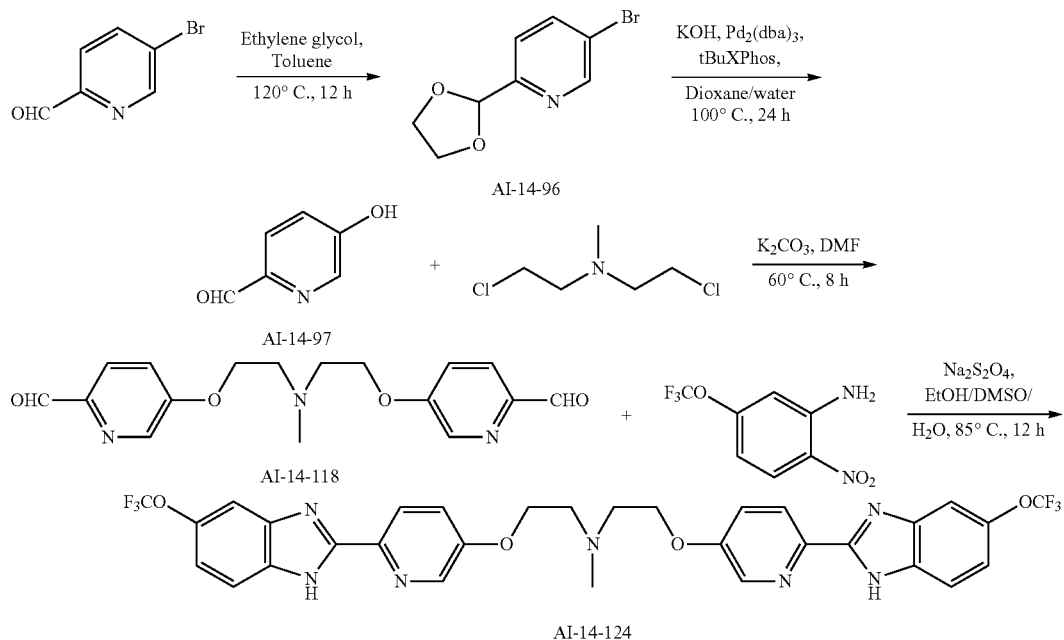

According to methods of the invention, the chemotherapeutic agent is selected from the group consisting of pirarubicin, aclarubicin, mitoxantrone, doxorubicin, daunorubicin, idarubicin, epirubicin and cytarabine, and mixtures thereof, or a pharmaceutically acceptable salt thereof.

As mentioned, a compound of formula (1) or a chemotherapeutic agent used in the invention may take the form of a "pharmaceutically acceptable salt", which refers to salts that retain the biological effectiveness and properties of the compounds of the invention and that are not biologically or otherwise undesirable. In many cases, the compounds administered in the methods of the invention are capable of forming acid and/or base salts by virtue of the presence of amino and/or carboxyl groups or groups similar thereto. Pharmaceutically acceptable acid addition salts may be prepared from inorganic and organic acids. Salts derived from inorganic acids include, but are not limited to, hydrochloric acid, hydrobromic acid, sulfuric acid, nitric acid, phosphoric acid, and the like. Pharmaceutically-acceptable base addition salts can be prepared from inorganic and Ara-C (cytarabine) and anthracyclines. Cytarabine is mainly used in the treatment of acute myeloid leukaemia, acute lymphocytic leukaemia and in lymphomas, where it is the backbone of induction chemotherapy. (Pigneux et al., 2007.) Cytarabine interferes with the synthesis of DNA, affecting rapidly dividing cells which require DNA replication for mitosis. The four most common anthracyclines are doxorubicin, daunorubicin, epirubicin and idarubicin. (McGowan et al., 2017.) Doxorubicin and daunorubicin were the first to be used in clinical practice. Epirubicin, a stereoisomer of doxorubicin, has an increased volume of distribution and longer half-life than doxorubicin. Idarubicin, a derivative of daunorubicin, is more lipophilic and has a higher cellular uptake than daunorubicin. Only a few more anthracyclines have attained clinical approval; these include pirarubicin, aclacinomycin A (aclarubicin), and mitoxantrone (a substituted aglyconic anthraquinone). (Minotti et al., 2004.). Despite extensive clinical utilization, the mechanisms of action of anthracyclines in cancer cells remain a matter of controversy. In a seminal commentary the following mechanisms were considered: 1) intercalation into DNA, leading to inhibited synthesis of macromolecules; 2) generation of free radicals, leading to DNA damage or lipid peroxidation; 3) DNA binding and alkylation; 4) DNA cross-linking; 5) interference with DNA unwinding or DNA strand separation and helicase activity; 6) direct membrane effects; 7) initiation of DNA damage via inhibition of topoisomerase II; and 8) induction of apoptosis in response to topoisomerase II inhibition (Gewirtz D. A., 1999.)

According to a method of the invention, the chemotherapeutic agent is doxorubicin or daunorubicin. For example, the chemotherapeutic agent is doxorubicin. In a method according to the invention, the chemotherapeutic agent is doxorubicin hydrochloride.

In a method according to the invention, a therapeutically effective combination of an amount of a compound of formula (1), such as compound (1a), and a chemotherapeutic agent, such as doxorubicin, is administered to synergistically inhibit proliferation of inv(16) leukemia cells. The term "inhibit" refers to the ability of a compound of the invention to reduce or impede a described function, such as cell proliferation. Preferably, inhibition is by at least 10%, more preferably by at least 25%, even more preferably by at least 50%, and most preferably, the function is inhibited by at least 75%.

In methods according to the invention, the synergistic combination used in the invention has a weight to weight ratio of the daily administered dose of chemotherapeutic agent to the daily administered dose of compounds of formula (1) ranging from about 0.0001:1 to 1000:1. The ratio may be from about 0.001:1 to about 100:1, e.g., from about 0.01:1 to about 10:1, e.g. from about 0.1:1 to about 1:1. Daily administration may be simultaneous, continuous or discontinuous.

Although a chemotherapeutic agent and a compound of formula (1) have been shown, separately, to be effective at inhibiting proliferation of inv(16) leukemia cells, when combined, the result is more than additive, it is synergistic. The amount of the synergistic combination of a compound of formula (1) and of chemotherapeutic agent or a salt thereof, required for use in a method of treatment according to the invention may vary with the route of administration, the nature of the condition being treated and the age and condition of the patient and will be ultimately at the discretion of the attendant physician or clinician. It is standard practice to treat acute myeloid leukemia patients with daunorubicin at doses of 45 to 50 mg per square meter of body-surface area for 3 days, plus cytarabine at a dose of 100 to 200 mg per square meter for 7 to 10 days. (Lowemberg, 2009.) In methods of treatment according to the invention, the daily administered dose of the chemotherapeutic agent is from about 10 mg/m$^2$ to about 10,000 mg/m$^2$. For example, one method of treatment includes administration of the chemotherapeutic agent at a daily dose of from about 20 to about 1000 mg/m$^2$. A method of treatment includes administration of the chemotherapeutic agent at a daily dose of about 25, 30, 45, 50, 100, 150, 250, 450, 750 or 900 mg/m$^2$. The administration of the chemotherapeutic agent can be made by intravenous infusion, intravenous push, bolus injection or subcutaneous injection. In methods of treatment according to the invention, daily administered dose of the compound of formula (1) is from about 10 mg/m$^2$ to about 10,000 mg/m$^2$. For example, one method of treatment includes administration of the compound of formula (1) at a daily dose of about 20 to about 1000 mg/m$^2$. One method of treatment includes administration of the compound of formula (1) at a daily dose of about 25, 30, 45, 50, 100, 150, 250, 450, 750 or 900 mg/m$^2$. In a method of treatment, the administration of the chemotherapeutic agent is once a day on days 1, 2 and 3, while the administration of the compound of formula (1) occurs once a day for one week, two weeks, three weeks, four weeks, five weeks, or more. The duration of administration of the compound of formula (1) may be determined by one of skill in the art, and continued as needed. In one method of treatment, the administration of the chemotherapeutic agent is once a day on days 1, and 2, while the administration of the compound of formula (1) occurs once a day for one week, two weeks, three weeks, four weeks, five weeks or more. In one method of treatment, the administration of the chemotherapeutic agent is once a day on day 1, while the administration of the compound of formula (1) occurs once a day for one week, two weeks, three weeks, four weeks, five weeks or more.

In methods of treatment according to the invention the compound of formula (1) and the chemotherapeutic agent are administered simultaneously, or sequentially by first administering the compound of formula (1) followed by administering the chemotherapeutic agent. In a method of treatment according to the invention, the compound of formula (1) and the chemotherapeutic agent may also be administered simultaneously. In an alternative method according to the invention, the compound of formula (1) and the chemotherapeutic agent may be administered sequentially by first administering the compound of formula (1) followed by administering the chemotherapeutic agent. According to other methods of treatment of the invention, additional therapeutically effective amounts of the compound of formula (1), may also be administered daily for 1 or more days, after administering the chemotherapeutic agent. For example, in a method of treatment according to the invention, a compound of formula (1) is administered, followed by administration of the chemotherapeutic agent, followed by daily administration of the compound of formula (1) for 1 or more days. As another example of a method of treatment of the invention, the compound of formula (1) and the chemotherapeutic agent are administered simultaneously, followed by daily administration of the compound of formula (1) for 1 or more days.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple injections.

In a method according to the invention, the extent of proliferation of cells from a subject suffering from inv(16) leukemia is measured using techniques known to those skilled in the art. A specific population of cells referred to as leukemia initiating cells using mouse models of inv(16) leukemia has been identified and accepted as an appropriate animal model. (Kuo, Y. H., et al., 2006.) This population of cells retains the inv(16) but does not possess the secondary mutations associated with disease. Upon acquisition of such secondary mutations, these cells can progress to overt leukemia. These cells are also typically more resistant to traditional cytotoxic chemotherapy and therefore represent a pool of cells from which relapse can occur. Cells may be extracted for measurement from blood, spleen, bone marrow, and/or spinal fluid. For example, populations of Lin-Sca-Kit+ cells extracted from a subject with inv(16) leukemia are measured using flow cytometry. The Lin-Sca1-c-Kit+ cell population, is enriched in the leukemia initiating cell (LIC) and leukemia stem cell (LSC) population.

In a method of treatment according to the invention, the compound of formula (1) and the chemotherapeutic agent are administered in a pharmaceutical composition comprising the compound of formula (1), the chemotherapeutic agent, and a pharmaceutically acceptable carrier. In other methods of treatment according to the invention, the compound of formula (1) is administered in a pharmaceutical composition comprising the compound of formula (1) and a pharmaceutically acceptable carrier, and the chemotherapeutic agent is subsequently administered in a pharmaceutical composition comprising the chemotherapeutic agent and a pharmaceutically acceptable carrier. In methods according to the invention, the dosage formulations of the pharmaceutical can be the same or different. For example, both the chemotherapeutic agent and the compound of formula (1) are formulated as solutions for parenteral delivery. Alternatively, the chemotherapeutic agent is formulated as a solution, and the compound of formula (1) is formulated as a tablet.

A separate embodiment of the invention is a pharmaceutical composition comprising a pharmaceutically-acceptable carrier and a therapeutically effective combination of
a) a compound of the formula (1)

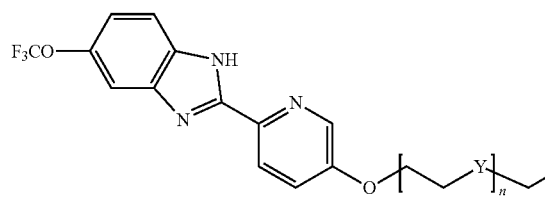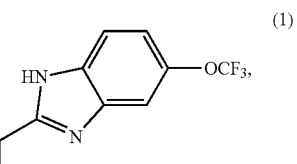

(1)

where Y is O, NH, or NR where R is methyl or ethyl,
n is an integer of from 1 to 10,
or a pharmaceutically acceptable salt thereof; and
b) a chemotherapeutic agent selected from the group consisting of pirarubicin, aclarubicin, mitoxantrone, doxorubicin, daunorubicin, idarubicin, epirubicin, cytarabine, or a pharmaceutically acceptable salt thereof;
wherein the compound of formula (1) and the chemotherapeutic agent are present in a combined amount synergistically effective to inhibit growth of inv(16) leukemia cells.

A pharmaceutical composition according to the invention may be in any pharmaceutical form which contains a synergistic combination of a compound of formula (1) and the chemotherapeutic agent. The pharmaceutical composition may be, for example, a tablet, a capsule, a liquid suspension, an injectable composition, a topical composition, an inhalable composition or a transdermal composition. Liquid pharmaceutical compositions may also be prepared. The pharmaceutical compositions generally contain, for example, about 0.1% to about 99.9% by weight of a combined amount of a compound of formula (1) and the chemotherapeutic agent, for example, about 0.5% to about 99% by weight of a combined amount of a compound of formula (1) and the chemotherapeutic agent and, for example, 99.5% to 0.5% by weight of at least one suitable pharmaceutical excipient. In one embodiment, the composition may be between about 5% and about 75% by weight of a combined amount of a compound of formula (1) and the chemotherapeutic agent with the rest being at least one suitable pharmaceutical excipient or at least one other adjuvant, as discussed below.

Depending on the type of pharmaceutical composition, the pharmaceutically acceptable carrier may be chosen from any one or a combination of carriers known in the art. The choice of pharmaceutically acceptable carrier depends upon the pharmaceutical form and the desired method of administration to be used.

Suitable liquid pharmaceutical compositions contain solubilizing agents that improve drug aqueous solubility, such as, for example, cyclodextrins. One non-limiting example of a cyclodextrin is a polyanionic variably substituted sulfobutyl ether of β-cyclodextrin (β-CD) (Captisol®).

For a solid pharmaceutical composition of the invention, the carrier in a solid pharmaceutical composition should not substantially alter either the compound of formula (1) or the chemotherapeutic agent. Nor should the carrier be otherwise incompatible with the compound of formula (1) nor the chemotherapeutic agent used, such as by producing any undesirable biological effect or otherwise interacting in a deleterious manner with any other component(s) of the pharmaceutical composition.

The pharmaceutical compositions of the invention may be prepared by methods known in the pharmaceutical formulation art, for example, see Remington's Pharmaceutical Sciences, 18th Ed., (Mack Publishing Company, Easton, Pa., 1990), which is incorporated herein by reference. Suitable solid dosage forms of the pharmaceutical composition of the invention include at least one pharmaceutically acceptable excipient such as, for example, sodium citrate or dicalcium phosphate or (a) (a) fillers or extenders, such as, for example, starches, lactose, sucrose, glucose, mannitol, and silicic acid, (b) binders, such as, for example, cellulose derivatives, starch, aliginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others, as is known in the pharmaceutical art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suitable suspensions may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Dosage forms for oral administration, which includes capsules, tablets, pills, powders, granules, and suspensions may be used. Suitable pharmaceutical compositions according to the invention may also be formulated as liquid or injectable pharmaceutical compositions. Administration may be carried out via any of the accepted modes of administration or agents for serving similar utilities. Thus, administration may be, for example, orally, buccally, or parenterally (intravenous, intramuscular, intraperitoneal, or subcutaneous), in the form of solid, semi-solid, lyophilized powder, or liquid dosage forms, such as, for example, tablets, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the condition to be treated.

Generally, in pharmaceutical compositions according to the invention, the combined concentration of the compound of formula (1) and the chemotherapeutic agent of the invention in a liquid composition, such as an injectable solution, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

EXAMPLES

Example 1: Leukemia Transplantation Studies in Mice

The experiments with animals were performed in accordance with a protocol reviewed and approved by the University of Massachusetts Institutional Animal Care and Use Committee. An efficient mouse model of inv(16)AML was used. (L. Xue, et al., 2014.) Leukemic cells carrying $Cbfb^{+/MYH11}$ and $Nras^{+/G12D}$ oncogenic alleles were generated in CD45.2 C57BL/6 mice, as previously described (Illendula, et al., 2015.) Briefly, $2 \times 10^3$ $Cbfb^{+/MYH11}$; $Nras^{+/G12D}$ leukemic cells were transplanted into each of 16 sub-lethally irradiated six to eight-week-old CD45.1 C57BL/6 female mice. Five days post-transplant, mice were placed in 4 groups with 4 mice in each group: DMSO (control, 50 µL), Dox, AI-10-49, and Dox+AI-10-49. Both Dox groups received a single dose of doxorubicin (2 mg/kg) 5 days post-transplant. Both AI-10-49 groups received a daily dose of AI-10-49 (200 mg/kg) in DMSO injected intraperitoneally for 10 days. After this 10-day period, all mice were sacrificed and analyzed for leukemia burden via several measures. Mice were kept under observation by more than one person to determine the median leukemia latency, and were euthanized once signs of disease were detected, including reduced motility and grooming activity, hunched back, pale paws (anemia), and hypothermia. At time of euthanasia, peripheral blood and spleen cells were extracted and analyzed as previously described (Y. H. Kuo, et al., 2006.). Leukemia burden was analyzed in peripheral blood by measuring the total white blood cell counts, the number of cells in the c-kit(+)-gated population, spleen weight and cell number, and spleen Lin-Sca1-c-kit+ population. For Kit+ and Lin-Sca-Kit+ results, flow cytometry was used to measure the effect.

The white blood cell count was measured as shown in FIG. 1. This was reduced in both AI-10-49 and Dox groups. The combination of Dox and AI-10-49 showed an additive effect in reducing the WBC.

Figure 2:
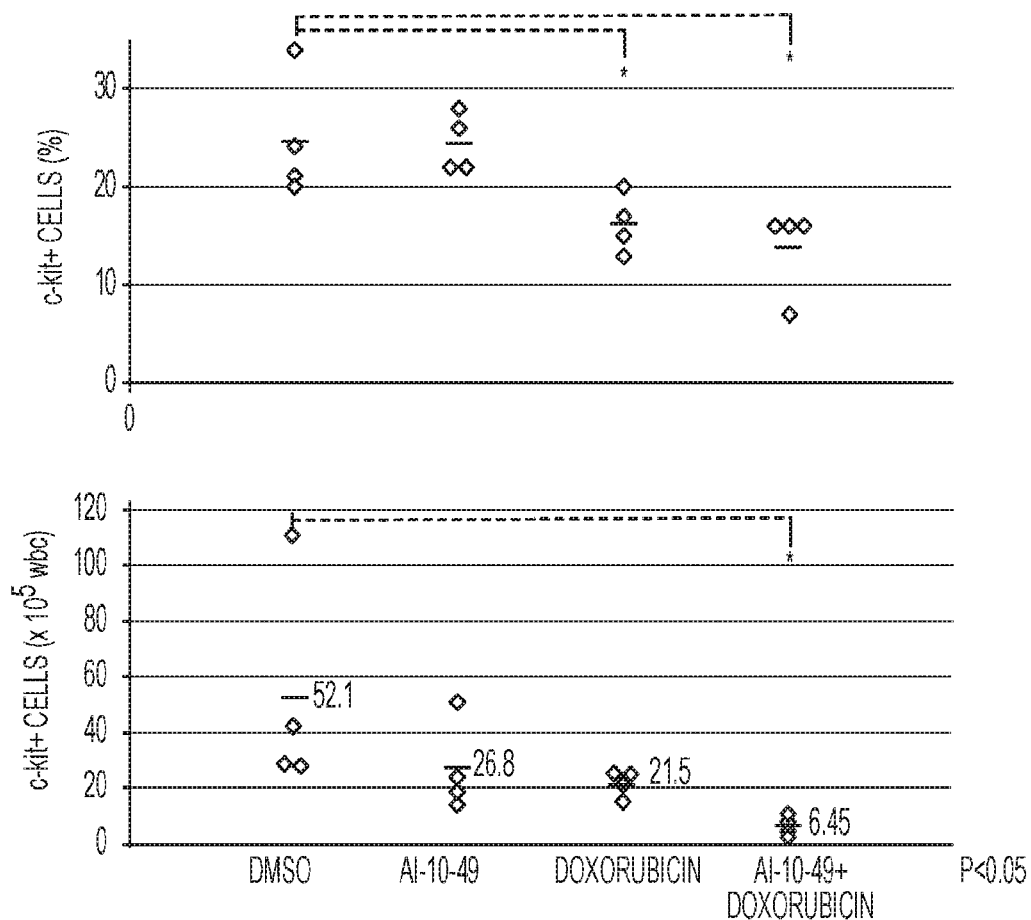
FIG. 2. Measurement of c-Kit+ cell population from mice transplanted with leukemia and treated with DMSO (control), doxorubicin, AI-10-49, and Doxorubicin+AI-10-49.

The c-Kit+ cell population was assessed as shown in FIG. 2. The c-Kit+ cell population is an enriched fraction containing the leukemic cells. Here, individual agents had an effect and the combination showed an additive effect.

Figure 3:
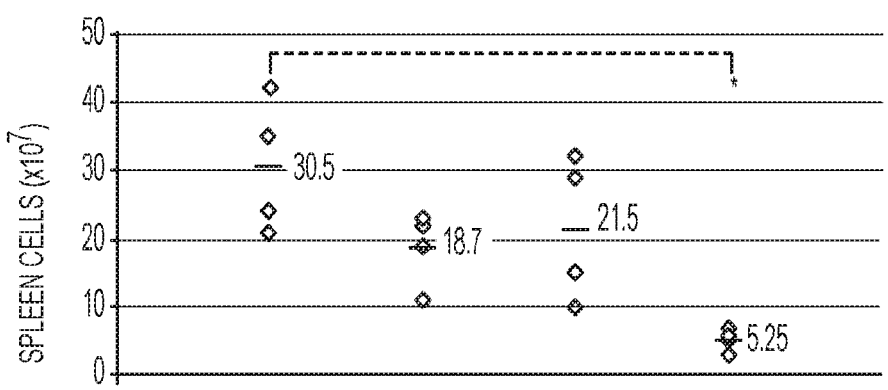
FIG. 3. Measurement of Spleen weight and cell number from mice transplanted with leukemia and treated with DMSO (control), doxorubicin, AI-10-49, and Doxorubicin+AI-10-49.
Figure 3:
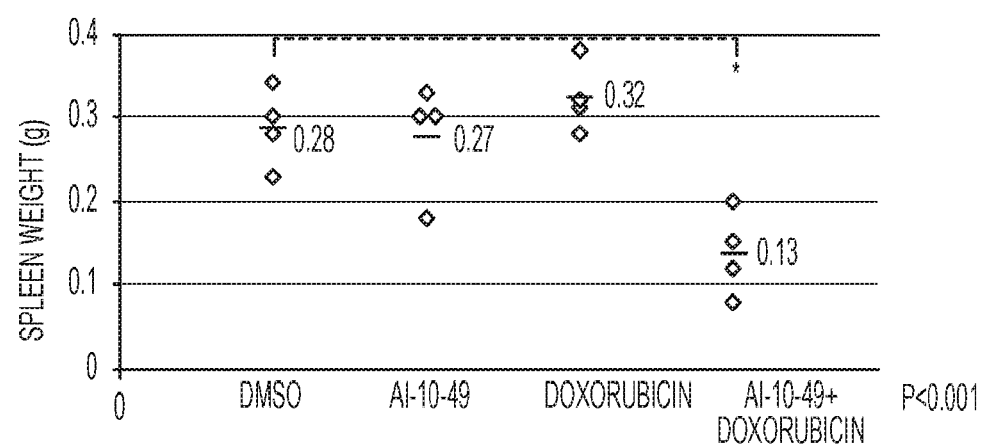

Spleen weight and cell number were evaluated as shown in FIG. 3. These are elevated in leukemia patients. Spleen cells showed a similar additive effect as seen for WBC and c-Kit+ cells and spleen weight showed a synergistic effect of the combination relative to either of the single agents.

Figure 4:
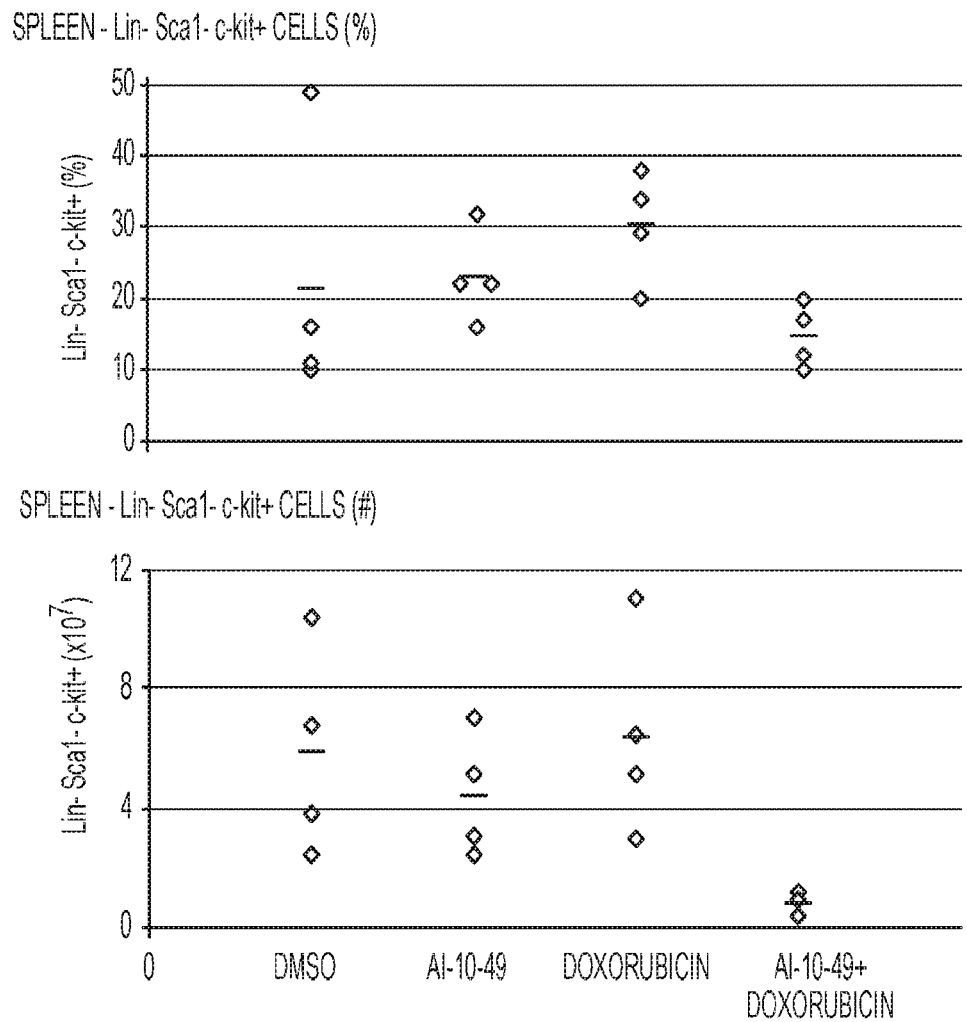
FIG. 4. Measurement Lin-Sca1-C-Kit+ cell population from mice transplanted with leukemia and treated with DMSO (control), doxorubicin, AI-10-49, and Doxorubicin+AI-10-49.

Finally, effects on the Lin-Sca1-c-Kit+ cell population are shown in FIG. 4. This cell population is enriched in the leukemia initiating cell (LIC) or leukemia stem cell (LSC). Here, a clear synergistic effect on the number of these cells was observed with Dox+AI-10-49 whereas only a modest effect was seen with AI-10-49 alone and no effect was seen with Dox alone.

As doxorubicin is a component of the current standard of care for inv(16) AML patients, we have shown an increase in efficacy by combining a targeted CBFβ-SMMHC inhibitor, AI-10-49, with doxorubicin. Taken together, these results argue strongly for the utility of combing AI-10-49 with doxorubicin in patients to improve outcomes. In particular, the last result argues that the combination can effectively target the LIC population which is the reservoir of leukemic cells that drives relapse. This argues strongly that the combination would improve outcomes for inv(16) AML patients.

Example 2: Effects on the Proliferation of the Inv(16)+ Cell Line ME-1

ME-1 cells (Inv(16)+)(DSMZ, Germany) were cultured in RPMI 1640 with 20% fetal bovine serum, and 25 mM HEPES. $5 \times 10^5$ ME-1 cells were cultured for 24 hours in DMSO, or different combinations with differing order of addition as indicated, using 96 well plates. Cells were incubated for a total of 4 days and proliferation was measured using the MTT kit, CellTiter 96® AQueous One Solution (Promega, Pa.). Compounds were added day 1 alone, day 2 alone, or both on day 1 to assess any effect of the timing of the combination. The experiments were replicated at least 2 times.

Figure 5:
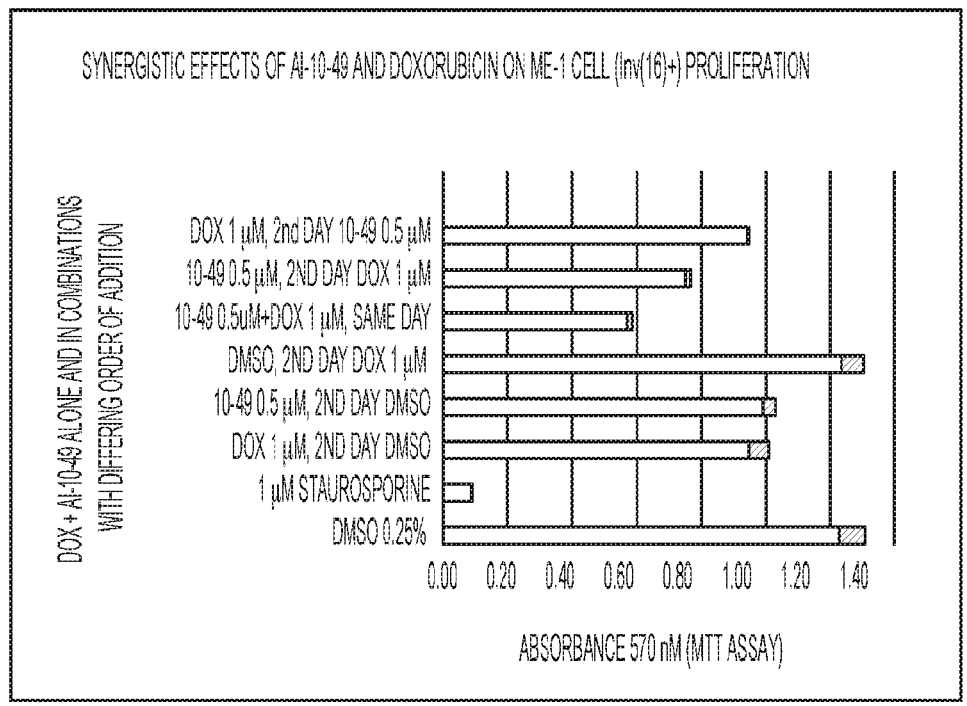
FIG. 5. Measurement of the effects of AI-10-49 and doxorubicin and combinations thereof against the ME-1 leukemia cell line which expresses the CBFβ-SMMHC fusion protein.

As shown in FIG. 5, synergy for the combination of AI-10-49+doxorubicin added simultaneously as well as for addition of AI-10-49 followed by doxorubicin on the second day was observed. Whereas addition of doxorubicin followed by AI-10-49 showed inhibition comparable to each component added separately.

Example 3: Synthesis of N-methyl-2-((6-(5-(trifluoromethoxy)-1H-benzo[d]imidazol-2-yl)pyridin-3-yl)oxy)-N-(2-((6-(5-(trifluoromethoxy)-1H-benzo[d]imidazol-2-yl)pyridin-3-yl)oxy)ethyl)ethan-1-amine, (AI-14-124)

The synthesis was achieved in two steps by previously described methods. (Illendula, et al., 2015.) In step 1, dialdehyde, 5,5'-(((methylazanediyl)bis(ethane-2,1-diyl))bis(oxy))dipicolinaldehyde (AI-14-118), was synthesized from commercially available intermediates, 5-hydroxypicolinaldehyde and 2-chloro-N-(2-chloroethyl)-N-methylethan-1-amine. The aldehyde thus synthesized was carried to next step. In Step 2, AI-14-124 was synthesized from nitroaniline (0.22 g, 1 mmol) and dialdehyde AI-14-118 (0.16 g, 0.5 mmol), in good yield (0.13 g, 40%). mp 139-142° C.; $^1$H NMR (800 MHz, CD$_3$OD-d$_4$): δ 2.54 (3H, s), 3.03-3.04 (2H, t), 4.30-4.31 (2H, t), 7.11 (1H, s), 7.40-7.60 (3H, m), 8.13-8.14 (1H, d, J=8.64 Hz), 8.36 (1H, d, J=3.3 Hz); $^{13}$C NMR (800 MHz, CD$_3$OD-d$_4$): δ 44.00, 57.40, 68.05, 105.91, 112.15, 118.11, 121.67, 122.75, 123.72, 134.48, 135.71, 139.64, 141.56, 146.49, 154.61, 157.67. HRMS: m/z [M+H]$^+$ calc'd for $C_{31}H_{25}F_6N_7O_4$; 674.1945; found: 674.1947.

REFERENCES

1. Illendula, A., Pulikkan, J. A., Zong, H., Grembecka, J., Xue, L., Sen, S., Zhou, Y., Boulton, A., Kuntimaddi, A., Gao, Y., Rajewski, R. A., Guzman, M. L., Castilla, L. H., Bushweller, J. H., (2015). *Science* 347, 779-784.
2. F. Ravandi, A. K. Burnett, E. D. Agura, H. M. Kantarjian, *Cancer* 110, 1900-1910 (2007).
3. Pulsoni, A., S. Iacobelli, et al., (2008). *Haematologica* 93(7): 1025-32.
4. Farag, S. S., K. J. Archer, et al., (2006). *Blood* 108(1): 63-73.
5. Nakano, Y., H. Kiyoi, et al., (1999). *Br J Haematol* 104(4): 659-64.
6. Kottaridis, P. D., R. E. Gale, et al., (2002). *Blood* 100(7): 2393-8.
7. Shih et al., (2008). *Leukemia* 22(2): 303-7.
8. Mammen, M., S. K. Choi, et al., (1998). *Angewandte Chemie-International Edition* 37(20): 2755-2794.
9. Kiessling, L. L., J. E. Gestwicki, et al., (2006). *Angewandte Chemie-International Edition* 45(15): 2348-2368.
10. Lukasik, S. M., L. Zhang, et al., (2002). *Nat Struct Biol* 9(9): 674-9.
11. Shigesada, K., B. van de Sluis, et al., (2004). *Oncogene* 23(24): 4297-307.
12. Mulder, A., T. Auletta, et al., (2004). *Journal of the American Chemical Society* 126(21): 6627-6636.
13. Pigneux, A., et al., *Haematologica* 2007, 92:1327-1334.
14. McGowan et al., *Cardiovasc Drugs Ther.* (2017) 31:63-75.
15. Minotti et al., (2004) *Pharmacol. Rev.* 56 (2): 185-229.
16. Gewirtz D. A., (1999) *Biochem Pharmacol* 57:727-741.
17. Lowemberg, B. et al., (2009), *NEJM* 361:1235-48.
18. Kuo, Y. H., et al., *Cancer Cell*, (2006) 9(1): p. 57-68.
19. L. Xue, J. A. Pulikkan, P. J. Valk, L. H. Castilla, *Blood* 124, 426-436 (2014).

The invention claimed is:
1. A method of treating inv(16) leukemia comprising the step of:
administering to a subject in need thereof a therapeutically effective combination of a) a compound of the formula (1)

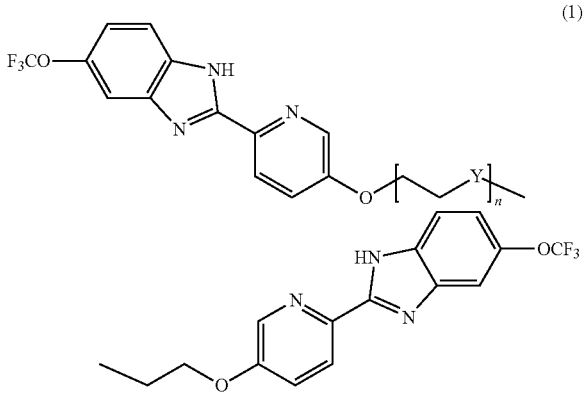

where Y is O, NH, or NR where R is methyl or ethyl, where n is an integer of from 1 to 10, or a pharmaceutically acceptable salt thereof; and
b) a chemotherapeutic agent selected from the group consisting of pirarubicin, aclarubicin, doxorubicin, daunorubicin, idarubicin, epirubicin, pharmaceutically acceptable salts and mixtures thereof;
wherein the therapeutically effective combination of the compound of formula (1) and the chemotherapeutic agent synergistically inhibits proliferation of inv(16) leukemia cells,
wherein the weight to weight ratio of the daily administered dose of the chemotherapeutic agent to the compound of formula (1) ranges from about 0.001:1 to about 100:1.
2. A method of claim 1, wherein Y is O.
3. A method of claim 1, wherein Y is N—CH$_3$.
4. A method of claim 1, wherein n is an integer from 1 to 5.
5. A method of claim 1, wherein the compound of formula (1) is selected from:

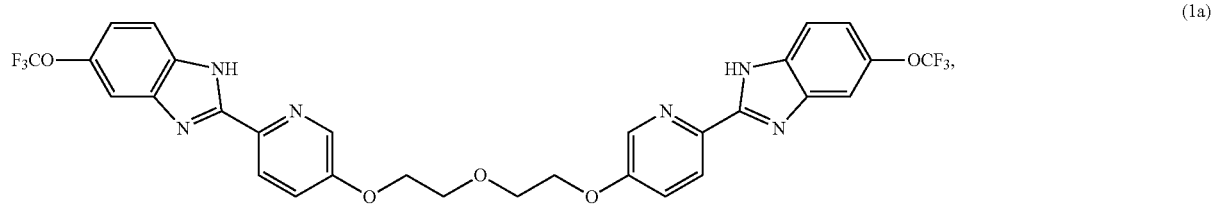

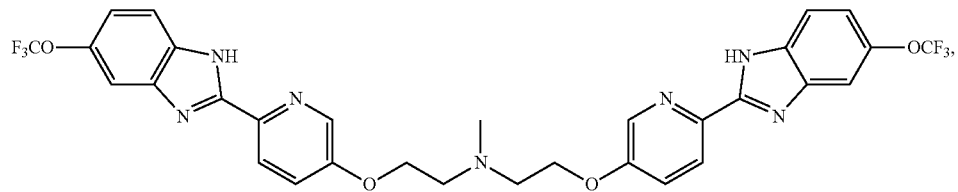
(1b)

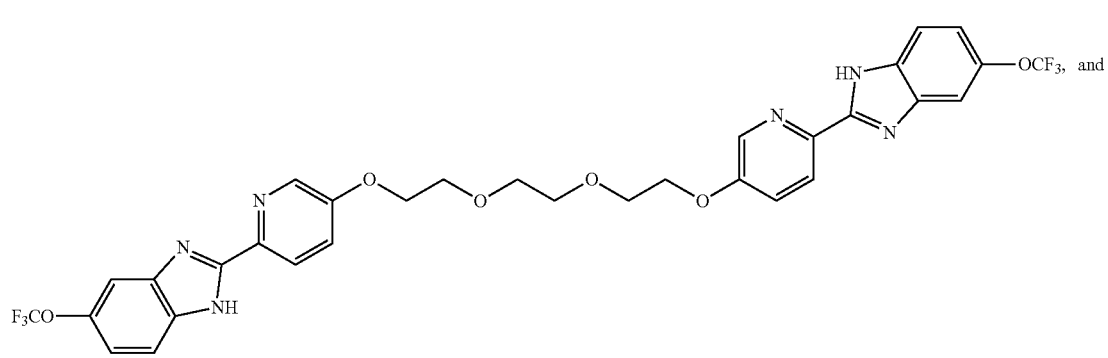
(1c), and (1d)

6. A method of claim 1, wherein the compound of formula (1) is:

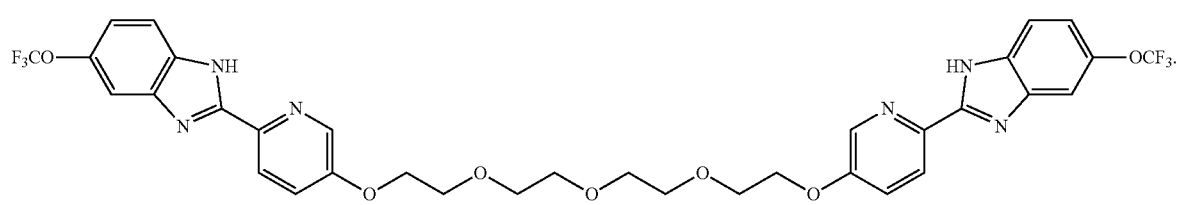
(1a)

7. A method of claim 1 wherein the compound of formula (1) and the chemotherapeutic agent are administered in a pharmaceutical composition comprising the compound of formula (1), the chemotherapeutic agent, and a pharmaceutically-acceptable carrier.

8. A method of claim 1, wherein the chemotherapeutic agent is doxorubicin or daunorubicin.

9. A method of claim 8, wherein the chemotherapeutic agent is doxorubicin.

10. The method of claim 1, wherein the inv(16) leukemia is acute myeloid leukemia.

11. A method of claim 1, wherein the compound of formula (1) and the chemotherapeutic agent are administered simultaneously, or sequentially by first administering the compound of formula (1) followed by administering the chemotherapeutic agent.

12. A method of claim 1, wherein the compound of formula (1) and the chemotherapeutic agent are administered simultaneously.

13. A method of claim 1, further comprising the step of administering additional therapeutically effective amounts of the compound of formula (1) daily for 1 or more days, after administering the chemotherapeutic agent.

14. A method of claim 1, further comprising the step of administering additional therapeutically effective amounts of the compound of formula (1) daily for 1 or more days, after simultaneously administering the compound of formula (1) and the chemotherapeutic agent.

15. A method of treating inv(16) leukemia comprising the step of: administering to a subject in need thereof a therapeutically effective combination of
 a) a compound of formula (1a) or a pharmaceutically acceptable salt thereof,

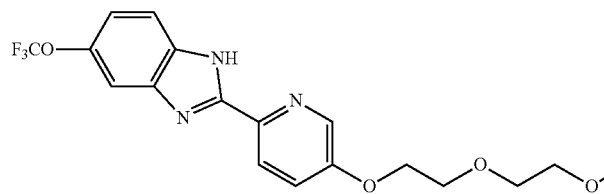
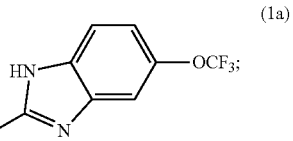

(1a)

and
b) doxorubicin or a pharmaceutically acceptable salt thereof;
wherein the therapeutically effective combination of the compound of formula (1a) and the doxorubicin synergistically inhibits proliferation of inv(16) leukemia cells,
wherein the weight to weight ratio of the daily administered dose of the doxorubicin to the compound of formula (1a) ranges from about 0.001:1 to about 100:1.

16. A pharmaceutical composition comprising:
a pharmaceutically-acceptable carrier and a therapeutically effective combination of:
a) a compound of the formula (1)

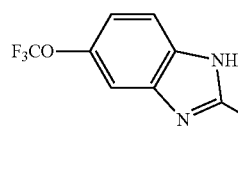
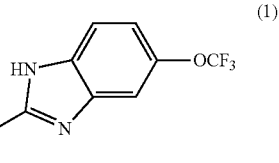

(1)

where Y is O, NH, or NR where R is methyl or ethyl,
where n is an integer of from 1 to 10,
or a pharmaceutically acceptable salt thereof; and
b) a chemotherapeutic agent selected from the group consisting of pirarubicin, aclarubicin, doxorubicin, daunorubicin, idarubicin, epirubicin, or a pharmaceutically acceptable salt thereof;
and a pharmaceutically acceptable excipient;
wherein the compound of formula (1) and the chemotherapeutic agent are present in a combined amount synergistically effective to inhibit proliferation of inv (16) leukemia cells,
wherein the weight to weight ratio of the daily administered dose of the chemotherapeutic agent to the compound of formula (1) ranges from about 0.001:1 to about 100:1.

17. A method of claim 15,
wherein the compound of formula (1a) and the doxorubicin are administered simultaneously, or sequentially by first administering the compound of formula (1a) followed by administering the doxorubicin.

18. A method of claim 17, wherein the compound of formula (1a) and the doxorubicin are administered simultaneously.

19. A method of claim 17, further comprising the step of administering additional therapeutically effective amounts of the compound of formula (1a) daily for 1 or more days, after administering the doxorubicin.

20. A method of claim 17, wherein the combination of formula (1a) and doxorubicin further comprises cytarabine or a pharmaceutically acceptable salt thereof.

21. A method of claim 1, wherein the weight to weight ratio of the daily administered dose of the chemotherapeutic agent to the compound of formula (1) ranges from about 0.01:1 to about 10:1.

22. A method of claim 21, wherein the weight to weight ratio of the daily administered dose of the chemotherapeutic agent to the compound of formula (1) ranges from about 0.1:1 to about 1:1.

23. A method of claim 15, wherein the weight to weight ratio of the daily administered dose of the doxorubicin to the compound of formula (1a) ranges from about 0.01:1 to about 10:1.

24. A method of claim 23, wherein the weight to weight ratio of the daily administered dose of the doxorubicin to the compound of formula (1a) ranges from about 0.1:1 to about 1:1.

25. A pharmaceutical composition of claim 16, wherein the weight to weight ratio of the daily administered dose of the chemotherapeutic agent to the compound of formula (1) ranges from about 0.01:1 to about 10:1.

26. A pharmaceutical composition of claim 25, wherein the weight to weight ratio of the daily administered dose of the chemotherapeutic agent to the compound of formula (1) ranges from about 0.1:1 to about 1:1.

* * * * *